United States Patent [19]

Konya et al.

[11] E Re. 29,826

[45] Reissued Nov. 7, 1978

[54] STABILIZED NON-MEDICAL FUNGICIDAL, BACTERICIDAL AND ALGICIDAL COMPOSITION

[75] Inventors: Kazumi Konya, Shimizu; Yoshihiro Konagai, Shizuoka; Makoto Muto; Hironari Sato, both of Shimizu; Yoshio Takahashi, Shizuoka, all of Japan

[73] Assignee: Kumiai Chemical Industry Co., Ltd., Tokyo, Japan

[21] Appl. No.: 839,758

[22] Filed: Oct. 5, 1977

Related U.S. Patent Documents

Reissue of:

[64] Patent No.: 4,022,605
Issued: May 10, 1977
Appl. No.: 590,074
Filed: Jun. 25, 1975

[30] Foreign Application Priority Data

Jun. 29, 1974 [JP] Japan ..... 49-74644

[51] Int. Cl.[2] ..... A01N 9/02

[52] U.S. Cl. ..... 71/67; 71/105; 71/106; 71/113; 71/115; 71/122; 106/15 R; 162/161; 210/62; 424/304; 424/311; 424/317; 424/318

[58] Field of Search ..... 71/67, 105, 118, 122, 71/106; 424/304

[56] References Cited

U.S. PATENT DOCUMENTS

| | | | |
|---|---|---|---|
| 2,853,449 | 9/1958 | Moudry et al. | 71/67 |
| 3,716,351 | 2/1973 | Kunkel et al. | 71/67 |
| 3,865,724 | 2/1975 | Shema et al. | 71/67 |

OTHER PUBLICATIONS

Burk et al., "Stable Liquid Antimicrobial Compositions, etc.;" (1972) CA 77 24628*b*. (1972).

Wolf et al., "2,2-Dibromo-3-nitrilopropionamide, etc;" (1972) CA 78 No. 25146*a*. (1973).

Exner et al., "Rates and Products of Decomp., etc.;" (1973) CA 79, No. 122495*s*. (1973).

*Primary Examiner*—Glennon H. Hollrah

*Attorney, Agent, or Firm*—Oblon, Fisher, Spivak, McClelland & Maier

[57] ABSTRACT

A halocyanoacetamide compound having the formula:

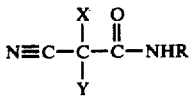

(I)

wherein X is a halogen such as Cl, F, Br and I;

Y represents a halogen such as chlorine, fluorine, bromine and iodine or hydrogen atom; and R represents a hydrogen atom or a lower alkyl group containing from 1 to 8 carbon atoms, is stabilized with an organic carboxylic acid or a diol.

8 Claims, No Drawings

STABILIZED NON-MEDICAL FUNGICIDAL, BACTERICIDAL AND ALGICIDAL COMPOSITION

Matter enclosed in heavy brackets [ ] appears in the original patent but forms no part of this reissue specification; matter printed in italics indicates the additions made by reissue.

BACKGROUND OF THE INVENTION

1. Field of the Invention

This invention relates to a stabilized non-medicinal fungicidal, bactericidal and algicidal composition which comprises a halocyanoacetamide compound.

2. Description of the Prior Art

Non-medicinal fungicidal and algicidal compositions are useful for inhibiting the growth of fungi, bacteria, yeasts, algae, and the like in industrial waters, such as the effluent from paper mills, or industrial cooling water; in cooling water for air-conditioners or in other materials such as metal processing lubricant oils, latex emulsions, aqueous emulsions, paper, wood, plywood, paints, pastes, pulps, fibers, and the like. However, the unlimited proliferation of such a microorganism can cause a decrease in product quality of can cause product damage. It can also result in long operation shutdowns or can otherwise cause severe economic loss.

The control of the proliferation of the microorganism in industrial waters is especially important in those systems that use large water recirculation systems, since such systems can become virtual breeding grounds for the growth of a wide variety of organisms. As the waters become increasingly contaminated, disposal becomes a worsening problem because discharge into waterways could cause pollution of rivers or the sea. Moreover, the unrestricted growth of microorganisms can cause clogging of pipes or can frustrate heat-exchange mechanisms due to the build-up of fungi, or bacteria, generally called slime and algae. Slime formed in an important part of apparatus, such as in a white water tank, a riffler wall or a screen in the paper and pulp industry can stain products thereby decreasing quality. Slime present in paper manufacturing can also cause tearing of the paper in the high speed processing machines. Such microorganism-caused difficulties can also occur in lubricant emulsion recycling systems commonly used in metal processing. In these systems, the proliferation of fungi or bacteria can result in rotting of the emulsion. In many other industries as well, such as those engaged in the production of paints, latex emulsions, fiber pastes, plywoods, etc., the proliferation of fungi or bacteria can be quite deleterious. Consequently, a need exists for a technique for preventing or controlling the proliferation of these microorganisms.

SUMMARY OF THE INVENTION

Accordingly, it is one object of this invention to provide a stabilized non-medical fungicidal, bactericidal and algicidal composition involving the prevention of difficulties caused by proliferation of these organisms in industrial wastes.

It is another object of this invention to provide a process for preparing a stabilized non-medical fungicidal, bactericidal and algicidal composition. These and other objects of this invention, as will hereinafter become more readily apparent from the ensuing discussion, have been attained by providing a composition which comprises as active ingredient a halocyanoacetamide having the formula (I)

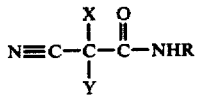

wherein X represents a halogen atom such as chlorine, fluorine, bromine and iodine and Y is such a halogen or hydrogen atom; and R represents a hydrogen atom or a lower alkyl group, containing from 1 to 8 carbon atoms and stabilizer of an organic carboxylic acid such as a dicarboxylic acid, an hydroxy carboxylic acid and a monocarboxylic acid and the like, or a diol containing up to 14 carbon atoms. The stabilized non-medicinal fungicidal, bactericidal and algicidal composition preferably comprises an halocyanoacetamide having the formula (I) and a haloacetic ester having the formula (II)

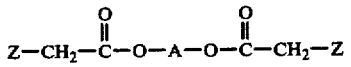

(II)

wherein Z represents a halogen such as fluorine, chlorine, bromine and iodine and A represents an alkylene or alkenylene group containing from 1–8 carbon atoms and a stabilizer of an organic carboxylic acid or a diol.

DETAILED DESCRIPTION OF THE PREFERRED EMBODIMENTS

Suitable halocyanoacetamides of the formula (I), include monochlorocyanoacetamide, monobromocyanoacetamide, dichlorocyanoacetamide, dibromocyanoacetamide, N-methyldibromocyanoacetamide, or the like. Suitable haloacetic esters of the formula (II) include 1,2-bis(bromoacetoxy) ethane, 1,2-bis(bromoacetoxy) propane, 1,2-bis(chloroacetoxy) ethane, 1,4-bis(bromoacetoxy)-2-butene. The combination of dibromocyanoacetamide and 1,4-bis(bromoacetoxy)-2-butene provides very high microbiocidal and algicidal effects. Suitable organic carboxylic acids and diols used for stabilizing compositions comprising a halocyanoacetamide having the formula (I) and a haloacetic ester of the formula (II), include organic acids such as succinic acid, salicylic acid, oxalic acid, α-tartaric acid, phthalic acid, fumaric acid, propionic acid, maleic acid, malonic acid, malic acid, bromoacetic acid, lactic acid, citric acid, formic acid, oleic acid and the like; and diols such as ethyleneglycol, 1,2-propanediol, 1,3-propanediol, 1,2-dihydroxybutane, 2,3-dihydroxybutane, 1,3-dihydroxybutane, 1,4-dihydroxy-2-butyne, 1,4-dihydroxy-2-butene, 1,5-dihydroxypentane, 1,6-dihydroxyhexane, 2,5-dihydroxyhexane, 1,7-dihydroxyheptane, 2,5-dihydroxy-(3)-hexene and the like. These stabilizers can be used for increasing the stability of the halocyanoacetamide used alone or in combination with a haloacetic ester. It is especially preferred for stabilization to use lactic acid or citric acid as the organic carboxylic acid or 1,4-dihydroxy-2-butene or [1,4-hydroxybutane] *1,4-dihydroxybutane* as the diol. The amount of the organic carboxylic acid or the diol employed is usually 0.01–10 wt. %, preferably 0.1–5 wt. % relative to the amount of the composition containing the halocyanoacetamide having the formula (I).

Additionally, it is preferred to use the halocyanoacetamide of formula (I) and the haloacetic ester of formula (II) in the form of an emulsion by adding a desirable solvent and a desirable surfactant. Suitable solvents include 1,1,1,-trichloroethane, xylene, polyols, ketones and the like. The preferred amount of the solvent is that sufficient to dissolve the active ingredients. When a surfactant is added, it is sometimes unnecessary to add a solvent since many surfactants can serve the purpose. The amount of the surfactant to be added depends upon the nature of the composition and is usually 0.01–20 wt. %, preferably 0.1–5 wt. %. The active ingredients can also be used in the form of a wettable powder by combining them with a mineral carrier such as bentonite, white clay, silica and the like, and with a surfactant. If the water to be treated is alkaline, it is preferred to add an acid to the water in order to neutralize it or to the composition itself.

When the water has an alkaline pH, the halocyanoacetamide of formula (I) is unstable by itself suffering a decrease in its effect within a short time. Accordingly, it has been difficult to obtain a desirable fungicidal, bactericidal and algicidal effect. Addition of an alkali metal halide has been proposed to improve the effect of the halocyanoacetamide. However, the results are unsatisfactory as shown in the tests described hereinafter. On the other hand, the haloacetic esters having the formula (II) have known activity for inhibiting the growth of fungi, bacteria, yeasts, algae, and the like. However, it is necessary to use these agents in high concentration. Accordingly, when used for slime control, there are significant disadvantages with respect to cost and capability for maintaining the effectiveness of the composition. As can clearly be seen from the above discussion, both compounds (I) and (II) have known disadvantages which make the probability for the successful use of either separately as an industrial microbiocide and algicide marginal at best. It is therefore quite surprising that the present inventors have now found that the combination of compounds (I) and (II) provides excellent microbiocidal and algicidal effects when formulated in a ratio of compound I: compound II; of 1:0.1–10, preferably 1:0.2–4, even in low concentrations. However, even in that combination, the halocyanoacetamide of formula (I) is disadvantageously unstable. But as indicated above, when stabilized by combination with an organic carboxylic acid or a diol, the halocyanoacetamide or formula (I) maintains its activity for a long period of time. Thus, when the compound (I) is combined with the haloacetic ester of formula (II), the synergistic effect mentioned above can be advantageously maintained.

The microbiocidal and algicidal compositions of the present invention are effective against a wide variety of fungi, such as Aspergillus niger, Penicillium steckii, Trichoderma, Geotrichum, and Candidum; bacteria, such as Aerobacter aerogenes or Bacillus subtilis; and the like. They can be used in low concentrations. (In such concentrations, each of the compounds would not impart fungicidal effects if used as in the prior art.) Consequently, the growth of noxious microorganisms in industrial waters can be completely inhibited with relatively small amounts of the composition. The composition of the present invention is therefore ideal for use as a slime control agent for inhibiting the proliferation of microorganisms, such as fungi, bacteria, yeasts, algae and the like, in recycled water systems, such as those used in paper or pulp mills and in cooling towers and the like. When the compounds (I) and (II) are combined in the above-mentioned ratios, the fungi, bacteria, yeasts and algae which cause the slime can be effectively inhibited in using only a low concentration of active ingredients.

Having generally described the invention, a more complete understanding can be obtained by reference to certain specific examples tests and experiments which are included for purposes of illustration only and are not intended to be limiting unless otherwise specified. In these examples, the terms "part" designates "parts by weight".

EXAMPLE 1

15 parts of dibromocyanoacetamide, 15 parts of 1,4-bis(bromoacetoxy)-2-butene, 43.5 parts of polyethyleneglycol (M.W. 200), 25 parts of 1,1,1-trichloroethane, 0.7 part of polyoxyethylene nonylphenyl ether, 0.3 part of calcium dodecylbenzenesulfonate and 0.5 part of 1,4-dihydroxy-2-butene as a stabilizer were mixed to form an emulsifiable concentrate.

EXAMPLE 2

15 parts of dibromocyanoacetamide, 15 parts of 1,4-bis(bromoacetoxy)-2-butene, 43.5 parts of polyethyleneglycol (M.W. 200), 25 parts of 1,1,1-trichloroethane, 0.7 part of polyoxyethylene nonylphenyl ether, 0.3 part of calcium dodecylbenzensulfonate and 0.5 part of 1,4-dihydroxybutane as a stabilizer were mixed to form an emulsifiable concentrate.

EXAMPLE 3

15 parts of dibromocyanoacetamide, 15 parts of 1,4-bis(bromoacetoxy)-2-butene, 1.7 parts of polyoxyethylene nonylphenyl ether, 0.3 part of calcium dinaphthylmethanedisulfonate, and 0.5 parts of 1,4-dihydroxybutane as a stabilizer and 67.5 parts of diatomaceous earth were mixed and crushed to form a wettable powder.

EXAMPLE 4

15 parts of dibromocyanoacetamide, 15 parts of 1,4-bis(bromoacetoxy)-2-butene, 43.5 parts of ethyleneglycol, 25 parts of 1,1,1-trichloroethane, 0.7 part of polyoxyethylene nonylphenyl ether, 0.3 part of calcium dodecylbenzenesulfonate and 0.5 part of lactic acid as a stabilizer were mixed to form an emulsifiable concentrate.

EXAMPLE 5

15 parts of dibromocyanoacetamide, 5 parts of 1,4-bis(bromoacetoxy)-2-butene, 53.5 parts of polyethyleneglycol (M.W. 200), 25 parts of 1,1,1-trichloroethane, 0.7 part of polyoxyethylene nonylphenyl ether, 0.3 part of calcium dodecylbenzenesulfonate and 0.5 part of 1,2-dihydroxyethane (stabilizer) were mixed to form an emulsifiable concentrate.

EXAMPLE 6

8 parts of dibromocyanoacetamide, 28 parts of 1,4-bis(bromoacetoxy)-2-butene, 27.5 parts of polyethyleneglycol (M.W. 200), 35 parts of 1,1,1-trichloroethane, 0.7 part of polyoxyethylene nonylphenyl ether, 0.3 part of calcium dodecylbenzenesulfonate and 0.5 part of 1,7-dihydroxyheptane (stabilizer) were mixed to form an emulsifiable concentrate.

EXAMPLE 7

20 parts of dibromocyanoacetamide, 78.5 parts of polyethyleneglycol (M.W. 200), 0.7 part of polyoxyethylene nonylphenyl ether, 0.3 part of calcium dodecylbenzenesulfonate and 0.5 parts of 1,4-dihydroxy-2-butene (stabilizer) were mixed to form an emulsifiable concentrate.

EXAMPLE 8

20 parts of dibromocyanoacetamide, 78.5 parts of polyethylene glycol (M.W. 200), 0.7 part of polyoxyethylene nonylphenyl ether, 0.3 part of calcium dodecylbenzenesulfonate and 0.5 part of 1,4-dihydroxybutane (stabilizer) were mixed to form an emulsifiable concentrate.

EXAMPLE 9

20 parts of dibromoacetamide, 1.7 parts of polyoxyethylene nonylphenyl ether, 0.3 part of calcium dodecylbenzenesulfonate, 3 parts of silica gel (white carbon No. 80), 74.5 parts of diatomaceous earth and 0.5 part of citric acid (stabilizer) were mixed and crushed to form a wettable powder.

TEST 1

20 parts of dibromocyanoacetamide, 0.7 part of polyoxyethylene nonylphenyl ether, 0.3 part of calcium dodecylbenzenesulfonate and 78.5 parts of polyethyleneglycol and the stabilizer shown in Table 1 were mixed to form emulsifible concentrates. The concentrates were stored at 40° C for 20 days in a cylinder. Thereafter, the stability of the compositions was measured by biological tests using the culture medium cloudiness method. The results are shown in Table 1.

Table 1

| Stabilizer | Concentration | Value of dibromoacetamide | Value 40° C, 20 days | Decomposition rate |
|---|---|---|---|---|
| succinic acid | 0.5 | 20.6 | 19.3 | 6.3 |
| oxalic acid | 0.5 | 20.0 | 19.0 | 5.0 |
| maleic acid | 0.5 | 20.1 | 19.2 | 4.5 |
| lactic acid | 0.5 | 21.0 | 30.3 | 3.3 |
| citric acid | 0.5 | 20.8 | 20.2 | 2.9 |
| 1,4-dihydroxybutane | 0.5 | 20.00 | 19.9 | 3.4 |
| 1,4-dihydroxybutene | 0.5 | 20.4 | 19.9 | 2.5 |
| Reference sodium iodide | 0.5 | 20.3 | 18.5 | 8.9 |
| none | — | 21.0 | 15.9 | 24.3 |

TEST 2

15 parts of dibromoacetamide, 15 parts of 1,4-bis(bromoacetoxy)-2-butene, 0.7 part of polyoxyethylene nonylphenyl ether, 0.3 part of sodium dodecylbenzenesulfonate, 43.5 parts of polyethyleneglycol (M.W. 200), 25 parts of 1,1,1-trichloroethane and 0.5 part of the stabilizers shown in Table 2 were mixed to form emulsifiable concentrates. The concentrates were stored at 40° C for 20 days in a cylinder. Thereafter, the stability of the compositions were measured by biological tests using the culture medium cloudiness method. The results are shown in Table 2.

Table 2

| Stabilizer | Concentration | Value of dibromoacetamide | Value 40° C 20 days | Decomposition rate |
|---|---|---|---|---|
| succinic acid | 0.5% | 14.2 | 13.2 | 7.0 |

Table 2-continued

| Stabilizer | Concentration | Value of dibromoacetamide | Value 40° C 20 days | Decomposition rate |
|---|---|---|---|---|
| salicylic acid | " | 14.8 | 13.6 | 8.1 |
| oxalic acid | " | 14.6 | 13.0 | 11.0 |
| α-tartaric acid | " | 14.6 | 13.4 | 8.2 |
| phthalic acid | " | 14.4 | 13.4 | 6.9 |
| fumaric acid | " | 14.2 | 13.0 | 8.5 |
| propionic acid | " | 14.2 | 13.5 | 4.9 |
| maleic acid | " | 14.3 | 13.3 | 7.0 |
| malonic acid | " | 14.3 | 13.3 | 7.0 |
| lactic acid | " | 14.2 | 14.3 | 6.3 |
| malic acid | " | 14.8 | 14.0 | 5.4 |
| bromoacetic acid | " | 14.3 | 12.6 | 11.9 |
| lactic acid | " | 14.6 | 14.2 | 2.7 |
| formic acid | 0.5% | 14.5 | 13.6 | 6.2 |
| oleic acid | " | 14.6 | 13.9 | 4.8 |
| citric acid | " | 14.7 | 14.4 | 2.0 |
| 1,2-dihydroxybutane | " | 14.3 | 13.1 | 8.4 |
| 1,3-dihydroxybutane | " | 14.6 | 13.2 | 9.6 |
| 1,4-dihydroxybutane | " | 14.5 | 14.1 | 2.8 |
| 2,3-dihydroxy butane | " | 14.5 | 13.6 | 6.2 |
| 1,4-dihydroxy-2-butyne | " | 14.3 | 13.2 | 7.7 |
| 1,4-dihydroxy-2-butyne | " | 14.8 | 14.2 | 4.1 |
| Reference sodium iodate | " | 14.7 | 13.0 | 9.1 |
| none | — | 14.2 | 9.1 | 35.9 |

TEST 3

15 parts of bromocyanoacetamide, 15 parts of 1,4-bis(bromoacetoxy)-2-butene, 0.7 part of polyoxyethylene nonylphenyl ether, 0.3 part of calcium dodecylbenzenesulfonate, 43.5 parts of polyethyleneglycol (M.W. 200), 25 parts of 1,1,1-trichloroethane and 0.5 part of the stabilizer shown in Table 3 were mixed to form emulsifiable concentrates. The concentrates were stored at 40° C for 20 days, and then the amount of 1,4-bis(bromoacetoxy)-2-butene was determined by the GLC method. The results are shown in Table 3.

Table 3

| Stabilizer | Concentration | Value of 1, 4-bis-(bromoacetoxy)-2-butene | Value 40° C 20 days | Decomposition rate |
|---|---|---|---|---|
| succinic acid | 0.5% | 14.8 | 14.6 | 1.4 |
| salicylic acid | " | 14.6 | 14.3 | 2.1 |
| oxalic acid | " | 15.0 | 14.8 | 1.3 |
| α-tartaric acid | " | 15.1 | 14.6 | 3.3 |
| phthalic acid | " | 15.0 | 14.3 | 4.7 |
| fumaric acid | " | 14.9 | 14.7 | 1.3 |
| propionic acid | " | 14.3 | 13.8 | 3.5 |
| maleic acid | " | 15.0 | 14.4 | 4.0 |
| malonic acid | " | 14.9 | 14.7 | 1.3 |
| lactic acid | " | 14.9 | 14.0 | 6.0 |
| malic acid | " | 15.1 | 14.7 | 2.6 |
| bromoacetic acid | " | 15.2 | 14.7 | 3.3 |
| lactic acid | " | 14.7 | 14.5 | 1.4 |
| formic acid | 0.5% | 14.9 | 14.3 | 4.0 |
| oleic acid | " | 14.7 | 14.3 | 2.7 |
| citric acid | " | 14.8 | 14.8 | 0 |
| 1,2-dihydroxybutane | " | 14.8 | 14.6 | 1.4 |
| 1,3-dihydroxybutane | " | 15.0 | 14.6 | 2.7 |
| 1,4-dihydroxybutane | " | 15.0 | 15.0 | 0 |
| 2,3-dihydroxybutane | " | 15.1 | 14.7 | 2.6 |
| 1,4-dihydroxy-2-butyne | " | 15.2 | 14.6 | 3.9 |
| 1,4-dihydroxy-2-butyne | " | 14.8 | 14.7 | 0.7 |
| Reference sodium iodate | " | 14.8 | 14.1 | 4.7 |
| none | — | 14.3 | 10.3 | 28.0 |

EXPERIMENT 1

Aerobacter aerogenes IAM 1102 which typically grows in a water system, was cultured in a broth liquid medium by shaking for 24 hours, and then was diluted 1,000 times. 1 ml of the diluted solution containing Aerobacter aerogenes was added to 18 ml of a fresh broth liquid medium contained in several 50 ml conical flasks closed with sterilized cotton. 1 ml portions of the solutions having the active ingredient concentrations as defined in Table 4, were added to the flasks. The flasks were shaken in a bath kept at 28° C. After 5, 15, 30, 90 and 180 minutes from the addition of the active ingredient, the concentrations of Aerobacter aerogenes in each broth liquid medium was measured to determine the fungicidal effects of the active ingredient. The results are shown in Table 4.

The compositions used for the experiments were as follows.

No. 1: Example 4 composition
No. 2: Example 5 composition
No. 3: Example 6 composition
No. 4: 40% dibromocyanoacetamide emulsifiable concentrate
No. 5: 30% dibromocyanoacetamide + 20% sodium iodide emulsifiable concentrate
No. 6: 60% 1,4-bis(bromoacetoxy)-2-butene
No. 7: none Table 4

| Composition | Conc. of active ingredient (ppm) | Time for contacting active ingredient (number of bacteria N/ml) | | | |
|---|---|---|---|---|---|
| | | 10 min | 30 min. | 90 min. | 180 min. |
| No. 1 | 6+ 6 | 4,000 | 200 | 10 | 0 |
| No. 2 | 9 + 3 | 3,500 | 600 | 50 | 10 |
| No. 3 | 2.6 + 9.1 | 6,000 | 800 | 100 | 10 |
| No. 4 | 15 | 28,000 | 74,000 | 82,000 | 100,000 |
| No. 5 | 15 + 10 | 28,000 | 68,000 | 50,000 | 68,000 |
| No. 6 | 20 | 100,000 | 98,000 | 90,000 | 310,000 |
| No. 7 | — | 520,000 | 680,000 | 1,100,000 | 1,300,000 |

Compound (I) or (II) when used alone with no stabilizer was not effective for inhibiting the growth of Aerobacter aerogenes in concentrations of 15–20 ppm. However, the combination of the two compounds imparted unexpectedly high fungicidal effects at the same concentrations.

EXPERIMENT 2

The growth inhibition concentrations of the compositions in the present invention as measured by the agar dilution method in a broth liquid medium (a pH of 7.5 in the case of bacteria and of 4.5 in the case of fungi) were measured. The results are shown in Table 5. The active ingredients used in the tests are defined in Experiment 1.

Table 5

| Composition | Growth inhibition minimum concentration (active ingredient ppm) | | | |
|---|---|---|---|---|
| | No. 1 | No. 4 | No. 5 | No. 6 |
| Acrobacter aerogenes | 6 | 100 | 100 | 75 |
| Bacillus subtillis | 6 | 100 | 100 | 50 |
| Escherichia Coli | 6 | 25 | 25 | 50 |
| Pseudomonas aeruginosa | 6 | 25 | 25 | 50 |
| Aspergillus niger | 12.5 | 200 | 200 | 100 |
| Penicillium steckii | 6 | 250 | 200 | 100 |
| Trichoderma SP | 6 | 200 | 200 | 150 |
| Geotrichum candidum | 6 | 150 | 150 | 75 |

As is clear from Table 5, compounds (I) or (II) are each much less effective when used alone with no stabilizer for the inhibition of bacteria, as when used in combination. The combinations themselves are quite effective against microorganisms which cause difficulties for industrial water systems and in industrial products, such as Aerobacter aerogenes, Bacillus subtilis, Escherichia coli, Pseudomonas aeraginosa, Aspergillus niger, Penicillium steckii, Trichoderma SP, Geotrichum cadidum.

EXPERIMENT 3

Fungicidal activites in white water under weak alkaline conditions

Into a 100 ml conical flask, was introduced 18 ml of white water containing 0.05–0.1% of pulp fibrils. The pH was adjusted to 8.1 and 2 ml of a diluted solution of the combination of the present invention containing concentrations of ingredients as shown in Table 6 were added. The mixture was continuously shaken at 30° C. After 30, 90 and 120 minutes from the addition of the diluted solution, 1 ml of white water was extracted from each flask and was uniformly mixed with 16 ml of MW medium and poured into a Petri dish having a diameter of 9 cm for solidification. Each of the microorganisms was cultured at 28° For 48 hours and the number in the colony in each Petri dish was counted to determine the fungicidal effect of the active ingredients. The results are shown in Table 6. The compositions are the same as those of Experiment 1.

Table 6

| Composition | Conc. of active ingredient (ppm) | Colony number in 1 ml of white water | | |
|---|---|---|---|---|
| | | 30 min. | 90 min. | 120 min. |
| No. 1 | 12.5 | 2,800 | 380 | 10 |
| No. 2 | " | 2,600 | 450 | 20 |
| No. 3 | " | 3,100 | 420 | 10 |
| No. 4 | " " | 650,000 | 130,000 | 6,600,000 |
| No. 5 | " | 460,000 | 110,000 | 3,600,000 |
| No. 6 | " | 1,000,000 | 840,000 | 420,000 |
| No. 7 | — | 43,000,000 | 27,000,000 | 83,000,000 |

EXPERIMENT 4

Cosmarium and Oscillatoria (algae) adhered onto a cooling tube were collected and cultured. Compositions thereof 5, 10, 50, 100, 150 and 200 ppm were prepared. The cultured Cosmarium or Oscillatoria was dipped into a diluted solution of the active ingredient of this invention for 1 hour, was removed and was also dipped into distilled water for 24 hours. The growth of Cosmarium or Oscillatoria was ascertained by separating the protoplasm thereof. The minimum effective concentration (ppm) of the active ingredient of the algicide was determined. The results are shown in Table 7. The compositions are the same as those used in Experiment 1.

Table 7

| Composition | No. 1 | No. 4 | No. 5 |
|---|---|---|---|
| Cosmarium | 5 | 200 | 50 |
| Oscillatoria | 5 | 200 | 100 |

Having now fully described the invention, it will be apparent to one of ordinary skill in the art that many changes and modifications can be made thereto without departing from the spirit or scope of the invention as set forth herein.

What is claimed as new and desired to be secured by letters patent of the United States is:

1. A stabilized microbiocidal composition which consists essentially of:

a microbiocidally effective amount of a halocyanoacetamide having the formula

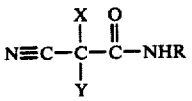

(I)

wherein

X represents a halogen atom;

Y represents a halogen atom or a hydrogen atom; and

R represents hydrogen atom or a lower alkyl group containing from 1 to 8 carbon atoms;

a stabilizer of a diol selected from the group consisting of ethylene glycol, 1,2-propanediol, 1,3-propanediol, 1,2-dihydroxybutane, 2,3-dihydroxybutane, 1,3-dihydroxybutane, *1,4-dihydroxybutane,* 1,4-dihydroxy-2-butyne, 1,4-dihydroxy-2-butene, 1,5-dihydroxypentane, 1,6-dihydroxyhexane, 2,5-dihydroxyhexane, 1,7-dihydroxyheptane and 2,5-dihydroxy-(3)-hexene, wherein the amount of stabilizer is 0.1 – 5 wt. % relative to the amount of halocyanoacetamide; and a solvent.

2. A stabilized microbiocidal composition which consists essentially of:

a microbiocidally effective amount of a halocyanoacetamide having the formula

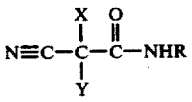

(I)

wherein

X represents a halogen atom;

Y represents a halogen atom or a hydrogen atom; and

R represents hydrogen atom or a lower alkyl group containing from 1 to 8 carbon atoms;

a stabilizer of a diol selected from the group consisting of ethylene glycol, 1,2-propanediol, 1,3-propanediol, 1,2-dihydroxybutane, 2,3-dihydroxybutane, 1,3-dihydroxybutane, *1,4-dihydroxybutane,* 1,4-dihydroxy-2-butyne, 1,4-dihydroxy-2-butene, 1,5-dihydroxypentane, 1,6-dihydroxyhexane, 2,5-dihydroxyhexane, 1,7-dihydroxyheptane and 2,5-dihydroxy-(3)-hexane, wherein the amount of stabilizer is 0.1 – 5 wt. % relative to the amount of halocyanoacetamide;

a solvent; and a haloacetic ester having the formula

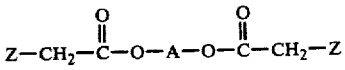

(II)

wherein

Z represents a halogen atom; and

A represents an alkenylene group containing up to 8 carbon atoms; wherein the ratio by weight of the halocyanoacetamide having the formula I to the haloacetic ester having the formula (II) is 1 : 0.1 – 10.

3. A method of treating water to inhibit the growth of microorganisms, which comprises adding a microbiocidally effective amount of the composition of claim 1 to said water.

4. A method of inhibiting the growth of microorganisms which comprises contacting said microorganism with a microbiocidally effective amount of the composition of claim 1.

5. A method for inhibiting the growth of slime in water which comprises adding a microbiocidally effective amount of the composition of claim 1 into said water.

6. A method of treating water to inhibit the growth of microorganisms, which comprises adding a microbiocidally effective amount of the composition of claim 2 to said water.

7. A method of inhibiting the growth of microorganisms which comprises contacting said microorganisms with a microbioligically effective amount of the composition of claim 2.

8. A method for inhibiting the growth of slime in water which comprises adding a microbiocidally effective amount of the composition of claim 2 in said water.

* * * * *